United States Patent
Swartout

(10) Patent No.: US 11,464,827 B2
(45) Date of Patent: Oct. 11, 2022

(54) ANTIVIRAL PHARMACEUTICAL COMPOSITIONS AND METHOD OF MANUFACTURING

(71) Applicant: ANEWSHA HOLDING GROUP LLC, San Juan, PR (US)

(72) Inventor: Chris Thomas Swartout, East Marion, NY (US)

(73) Assignee: Anewsha Holding Group LLC, San Juan, PR (US)

( * ) Notice: Subject to any disclaimer, the term of this patent is extended or adjusted under 35 U.S.C. 154(b) by 0 days.

(21) Appl. No.: 17/198,015

(22) Filed: Mar. 10, 2021

(65) Prior Publication Data

US 2021/0283216 A1 Sep. 16, 2021

Related U.S. Application Data

(60) Provisional application No. 62/987,855, filed on Mar. 10, 2020.

(51) Int. Cl.
| | |
|---|---|
| *A61K 36/00* | (2006.01) |
| *A61K 38/16* | (2006.01) |
| *A61K 31/05* | (2006.01) |
| *A61K 47/26* | (2006.01) |
| *A61K 36/04* | (2006.01) |
| *A61K 9/00* | (2006.01) |
| *A61K 9/20* | (2006.01) |
| *A61K 31/245* | (2006.01) |

(52) U.S. Cl.
CPC .......... *A61K 38/168* (2013.01); *A61K 9/0053* (2013.01); *A61K 9/2018* (2013.01); *A61K 31/05* (2013.01); *A61K 31/245* (2013.01); *A61K 36/04* (2013.01); *A61K 47/26* (2013.01)

(58) Field of Classification Search
CPC ................................ A61K 47/36; A61K 36/04
See application file for complete search history.

(56) References Cited

U.S. PATENT DOCUMENTS

| 7,118,765 | B2 | 10/2006 | Norman et al. | |
|---|---|---|---|---|
| PP33,143 | P2 | 6/2021 | Swartout et al. | |
| 2017/0273903 | A1* | 9/2017 | Bachmann | A23G 4/068 |
| 2018/0369191 | A1* | 12/2018 | Muscarella | A61K 31/05 |
| 2019/0091144 | A1* | 3/2019 | McGarrah | A23K 40/25 |

FOREIGN PATENT DOCUMENTS

| NL | 2009671 C * | 4/2014 | ............... A61P 31/12 |
|---|---|---|---|
| WO | WO-2018104950 A1 * | 6/2018 | ........... A61K 31/167 |

OTHER PUBLICATIONS

Mateu et al, Emergence of Herpes Simplex Virus-1 Syncytial Variants With Altered Virulence for Mice After Selection With a Natural Carrageenan. Sexually Transmitted Diseases, (Jun. 2011) vol. 38, No. 6, pp. 555-561 (Year: 2011).*
Lusvarghi & Bewley, "Griffithsin: An Antiviral Lectin with Outstanding Therapeutic Potential," Viruses 8(10):296, pp. 1-18 (Oct. 2016).
"(CBDRA60) to Prevent or Reduce Symptoms of COVID-19 and Prevention of Post-Acute Sequelae of SARS-CoV-2 Infection PASC," ClinicalTrials.gov, available at clinicaltrials.gov/ct2/show/record/NCT04777981 (first posted Mar. 2, 2021) [14 pages].

* cited by examiner

*Primary Examiner* — Qiuwen Mi
(74) *Attorney, Agent, or Firm* — McDonnell Boehnen Hulbert & Berghoff LLP

(57) ABSTRACT

The present disclosure provides compositions comprising combinations of one or more lectins, sulfated polysaccharides from marine algae, and cannabinoids and a pharmaceutically acceptable excipient or mixtures of excipients and methods of preparing such compositions.

16 Claims, No Drawings

ANTIVIRAL PHARMACEUTICAL COMPOSITIONS AND METHOD OF MANUFACTURING

CROSS REFERENCE TO RELATED APPLICATIONS

This application claims priority to U.S. Provisional Patent Application No. 62/987,855, filed Mar. 10, 2020, the contents of which is hereby incorporated by reference in its entirety.

BACKGROUND OF DISCLOSURE

Field

The present disclosure provides oral formulations comprising lectins, sulfated polysaccharides, cannabinoids, and/or osteltamivir phosphate and pharmaceutically acceptable excipients, and combinations thereof. The lectins can be, for example, a wild type lectin termed BanLec, isolated from the ripened fruit of the banana (Musa acuminate cultivars) and/or a red algae derived griffithsin (GRFT) protein. The sulfated polysaccharides can be from marine algae (e.g., *Gigartina* red algae). The present disclosure also provides methods of preparing formulations that are designed to dissolve in the oral cavity of the subject or be ingested with stabilized oral suspension formulas.

Technical Background

The lectin termed BanLec, isolated form the ripened fruit of the banana (Musa acuminate cultivars), exists as a dimer with a molecular mass of approximately 30 kDA. It is a member of the jacalin related lectin family and can recognize high mannose structures. Lectins in this family are characterized by the presence of a β-prism 1 structure composed of three Greek Key turn motifs. Greek Keys 1 and 2 are both involved in binding carbohydrates and contain a GXXXD binding motif, whereas Key 3 does not contain the binding motif. However this loop can assist ligand binding and determine lectin specificity. Griffithsin is a potent antiviral protein derived from red algae or Cnidarian phylum with activity against HIV, HCV, HSV 1 and HSV 2, SARS-CoV, Mers and other coronaviruses. Griffithsin (GRFT), an algae-derived lectin, is one of the most potent viral entry inhibitors discovered to date. It is currently being developed as a microbicide with broad-spectrum activity against several enveloped viruses. GRFT can inhibit human immunodeficiency virus (HIV) infection at picomolar concentrations, surpassing the ability of most anti-HIV agents. The potential to inhibit other viruses, including coronaviruses as well as parasites has also been demonstrated. Griffithsin's antiviral activity stems from its ability to bind terminal mannoses present in high-mannose oligosaccharides and crosslin these glycans on the surface of the viral envelope glycoproteins. This lectin combination has high efficacy, low toxicity and high binding affinity to act as an effective anti-viral against viruses as diverse as, for example, human immunodeficiency virus (HIV), Ebola, yellow fever, Zika, influenza, and coronaviruses (severe acute respiratory syndrome [SARS-CoV, SARS-CoV2] and Middle East respiratory syndrome [MERS-CoV]), respectively. The severe acute respiratory syndrome coronavirus 2 (SARS-CoV2) is the virus that causes the disease COVID-19. Though these viruses are taxonomically and genetically distinct, they are all enveloped viruses and therefore possess a lipid bilayer that protects the viral capsid and genetic material that is inside the viral particle. Additionally, several sulfated seaweed polysaccharides from *Gigartina skotsbergii* have shown high antiviral activity against enveloped viruses, including important human pathogens such as human immunodeficiency virus, herpes simplex virus, human cytomegalovirus, dengue virus and respiratory syncytial virus.

Enveloped viruses have surface glycoproteins that mediate attachment and fusion with the target cell membrane. These proteins constitute the first encounter with the host and the most exposed target that the immune system can attack; hence viruses have evolved to hide the features that would make them more susceptible to antibody neutralization. These strategies include hiding fundamental structural motifs through oligomerization or conformational occlusion, rapid mutation rates that lead to high sequence variability in non-essential regions such as variable loops, and extensive posttranslational glycosylation.

Thus, there is a need for new and improved formulations for patient use of these antiviral compounds. Described herein are dosage formulations containing combinations of cannabinoids, lectins, marine algae containing sulfated polysaccharides, and/or osteltamivir phosphate as active ingredients for targeted fast acting therapeutic use against enveloped viruses. The formulations of the disclosure can be administered orally, and in some embodiments, rapidly dissolve in the oral cavity, thus increasing the bioavailability of the antiviral compound. The formulations also have favorable organoleptic properties, making them tolerable to consume by dissolving in the mouth.

BRIEF SUMMARY OF THE DISCLOSURE

The present disclosure relates to oral compositions comprising lectins, sulfated polysaccharides, cannabinoids and a pharmaceutically acceptable excipient or mixture of excipients and methods of making the compositions.

One aspect of the present disclosure provides a composition comprising one or more lectins (e.g., GRFT and/or BanLec) and a cannabinoid and a pharmaceutically acceptable excipient or mixtures of excipients, or combinations thereof. Another aspect of the present disclosure provides a composition comprising one or more sulfated polysaccharides from marine algae (e.g., *Gigartina* red algae), a cannabinoid and a pharmaceutically acceptable excipient or mixtures of excipients, or combinations thereof.

In some embodiments of the disclosure, the lectins are griffithsin and banana lectin. In some embodiments, the sulfated polysaccharide is isolated from red algae or contained in whole red algae. In some embodiments of the disclosure, the cannabinoid is tetrahydrocannabinol (THC), delta-9-tetrahydrocannabivarin (THCv), 10-Ethoxy-9-hydroxy-delta-6a-tetrahydrocannabinol, 8,9-dihydroxy-delta-6a-tetrahydrocannabinol, delta-8-tetrahydrocannabinol, delta-8-tetrahydrocannabinolic acid, delta-9-tetrahydrocannabinol-C4 (THC-C4), delta-9-tetrahydrocannabinoic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorolic acid (THCA-C1), delta-9-tetrahydrocannabivarinic acid (THCVA), 10-Oxo-delta-6a-tetrahydrocannabinol (OTHC), dehydrocannabifuran (DCBF), delta-9-ci s-tetrahydrocannabinol (cis-THC), trhydroxy-delta-9-tetrahydrocannabinol (triOH-THC), 3,4,5,6,-tetrahydro-7-hydroxy-alpha-alpha-2-trimethyl-9-n-propyl-2, cannabidiol (CBD), cannabinol (CBN), cannabichromene (CBC), cannabichromenic acid (CBCA), cannabicyclol (CBL), cannabicyclolic acid (CBLA), cannabicyclovarin (CBLV), cannabivarin (CBV), Cannabidivarin (CBDVa), cannabinodiol (CBND), cannabielsion (CBE), cannabicyclol (CBL), cannabicyloic acid (CBLA), cannabitriol (CBT), cannabidiol monomehylerther (CBDM), cannabidiolic acid (CBDA), cannabidiorcol (CBD-C1), cannabielsoic acid B (CBEA-B), cannabielsin (CBE), cannabielsoin acid A (CBEA-A), cannabigerol (CBG), cannabigerol monomethlether (CBGM), cannabigerolic acid (CBGA), cannabigerolic acid (CBGA), cannabigerolic acid monomethlether (CBGAM), cannabigerovarin (CBGV), cannabigerovarinic acid (CBGVA), cannabinodiol (CBND), cannabinodivarin (CBVD), cannabinol (CBN), cannabinol methlether (CBNM), cannabinol-C2 (CBN-C2), cannabinol-C4 (CBN-C4), cannabinolic acid (CBNA), cannabiorcool (CBN-C1), cannabivarin (CBV), cannaitriol (CBT), cannabitriolvarin (CBTV), cannabichromanon (CBCF), cannabifuran (CBF), cannabiglendol (OH-iso-HHCV), cannabiripsol (CBR), cannbicitran (CBT), or 6-methano-2H-1-benzoxocin-5-methanol.

In some embodiments of the disclosure, the composition further comprises osteltamivir phosphate.

In other embodiments of the disclosure, the cannabinoid comprises a cannabidiol or tetrahydrocannabinol isolate. In yet other embodiments of the disclosure, the cannabinoid is a hemp-derived cannabidiol.

In some embodiments of the disclosure, the cannabinoid is in the range of from about 25 mg to about 120 mg per solid dosage form (e.g., tablet) or 60 mg per 360 ml for oral suspension formulation.

In some embodiments of the disclosure, the composition comprises griffithsin, banana lectin and a cannabinoid that is a mixture of one or more cannabinoid compounds (e.g., a mixture of CBG and CBD).

In some embodiments of the disclosure, the composition comprises an excipient that is a co-processed carbohydrate containing mannitol and sorbitol in a 2:1 ratio.

In some embodiments of the disclosure, the composition further comprises a taste enhancing agent and a lubricant. In other embodiments of the disclosure, the composition comprises an excipient that is one or more sugar alcohols.

In some embodiments of the disclosure, the composition dissolves in the oral cavity or is taken as an oral suspension formula.

In other embodiments of the disclosure, the composition further comprises a terpene.

Another aspect of the disclosure proves a tablet comprising a rapidly dissolving oral composition comprising an effective amount of GRFT, BanLec, a cannabinoid and a pharmaceutically acceptable excipient or mixtures of excipients.

Yet another aspect of the disclosure proves a tablet comprising a rapidly dissolving oral composition comprising red algae containing sulfated polysaccharides, a cannabinoid, and a pharmaceutically acceptable excipient or mixtures of excipients.

In some embodiments of the disclosure, the solid dosage form is a tablet that has a total weight of about 100 mg to about 800 mg, 550 mg to about 750 mgs, or about 600 to about 1000 mgs. In other embodiments of the disclosure, the oral suspension formulation has active ingredients in a concentration of 60 mg in a 360 ml of the oral suspension formula.

In some embodiments of the disclosure, the composition has favorable organoleptic properties or is tasteless.

Yet another aspect of the disclosure provides a method for preparing a rapidly dissolving oral composition comprising: (i) preparing a mixture of powder comprising one or more lectins (e.g., GRFT and/or BanLec) and a cannabinoid; (ii) blending the ingredients prepared in step (i) with at least one tableting excipient; and (iii) compressing the blend of step (ii) into a tablet.

Yet another aspect of the disclosure provides a method for preparing a rapidly dissolving oral composition comprising: (i) preparing a mixture of powder comprising marine algae (e.g., *Gigartina* red algae) and a cannabinoid; (ii) blending the ingredients prepared in step (i) with at least one tableting excipient; and (iii) compressing the blend of step (ii) into a tablet.

In some embodiments, the tableting excipient comprises a binder, a filler, optionally, a taste enhancing agent, a disintegrant, and/or a lubricant. In other embodiments, the tableting excipient is a co-processed carbohydrate containing mannitol and sorbitol in a 2:1 ratio.

In some embodiments, the tablet or oral suspension formulation comprises one or more lectins (e.g, GRFT and/or BanLec) or one or more sulfated polysaccharides from marine algae and one or more cannabinoids.

DETAILED DESCRIPTION OF THE DISCLOSURE

For the purposes of promoting an understanding of the principles of the present disclosure, reference will now be made to specific embodiments and specific language will be used to describe the same.

Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

It will be further understood that a number of aspects and embodiments are disclosed. Each of these has individual benefit and each can also be used in conjunction with one or more, or in some cases all, of the other disclosed aspects and embodiments, whether specifically delineated or not. Accordingly, for the sake of clarity, this description will refrain from repeating every possible combination of the individual aspects and embodiments in an unnecessary fashion. Nevertheless, the specification and claims should be read with the understanding that such combinations are implicitly disclosed, and are entirely within the scope of the disclosure and the claims, unless otherwise specified.

New formulations of rapidly dissolving tablets or oral suspension formulas containing active ingredients such as lectins (e.g., griffithsin and/or banana lectin), sulfated polysaccharides (e.g., sulfated polysaccharides isolated from red algae or contained in whole red algae), and cannabinoids for targeted fast acting therapeutic use, to be taken in the oral cavity and to quickly dissolve and increase bioavailability, are described herein. This disclosure further relates to a direct compression molecular binding tablet or oral suspension dosage forms of compositions comprising one or more lectins (e.g., griffithsin or banana lectin) and/or one or more sulfated polysaccharides (e.g., from red algae *Gigartina*) and one or more cannabinoids, such as tetrahydrocannabinols (THCs), including delta-9-tetrahydrocannabivarin (THCv), 10-Ethoxy-9-hydroxy-delta-6a-tetrahydrocannabinol, 8,9-dihydroxy-delta-6a-tetrahydrocannabinol, delta-8- tetrahydrocannabinol, delta-8-tetrahydrocannabinolic acid, delta-9-tetrahydrocannabinol-C4 (THC-C4), delta-9-tetrahydrocannabinoic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorolic acid (THCA-C1), delta-9-tetrahydrocannabivarinic acid (THCVA), 10-Oxo-delta-6a-tetrahydrocannbinol (OTHC), dehydrocannbifuran (DCBF), delta-9-cis-tetrahydrocannabinol (cis-THC), trhydroxy-delta-9-tetrahydrocannabinol (triOH-THC), 3,4,5,6,-tetrahydro-7-hydroxy-alpha-alpha-2-trimethyl-9-n-propyl-2, or cannabidiols (CBDs), including cannabinol (CBN), cannabichromene (CBC), cannabichromenic acid (CBCA), cannabicyclol (CBL), cannabicyclolic acid (CBLA), cannabicyclovarin (CBLV), cannabivarin (CBV), Cannabidivarin (CBDVa), cannabinodiol (CBND), cannabielsion (CBE), cannabicyclol (CBL), cannabicyloic acid (CBLA), cannabitriol (CBT), cannabidiol monomehylerther (CBDM), cannabidiolic acid (CBDA), cannabidiorcol (CBD-C1), cannabielsoic acid B (CBEA-B), cannabielsin (CBE), cannabielsoin acid A (CBEA-A), cannabigerol (CBG), cannabigerol monomethlether (CBGM), cannabigerolic acid (CBGA), cannabigerolic acid (CBGA), cannabigerolic acid monomethlether (CBGAM), cannabigerovarin (CBGV), cannabigerovarinic acid (CBGVA), cannabinodiol (CBND), cannabinodivarin (CBVD), cannabinol (CBN), cannabinol methlether (CBNM), Cannabinol-C2 (CBN-C2), Cannabinol-C4 (CBN-C4), cannabinolic acid (CBNA), cannabiorcool (CBN-C1), cannabivarin (CBV), cannaitriol (CBT), cannabitriolvarin (CBTV), cannabichromanon (CBCF), cannabifuran (CBF), cannabiglendol (OH-iso-HHCV), cannabiripsol (CBR), cannbicitran (CBT), or 6-methano-2H-1-benzoxocin-5-methanol as active ingredients.

Definitions

Articles "a" and "an" are used herein to refer to one or to more than one (i.e. at least one) of the grammatical object of the article. By way of example, "an element" means at least one element and can include more than one element.

As used herein, the term "and/or" includes any and all combinations of one or more of the associated listed items. It will be further understood that the use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as 1 mg to 5 mg, it is intended that values such as 2 mg to 40 mg, 10 mg to 30 mg, or 1 mg to 3 mg, etc., are expressly enumerated in this specification. These are only examples of what is specifically intended, and all possible combinations of numerical values between and including the lowest value and the highest value enumerated are to be considered to be expressly stated in this disclosure.

The term "about" in association with a numerical value means that the numerical value can vary plus or minus by 5% or less of the numerical value.

One aspect of the disclosure provides an oral composition (e.g., a solid dosage form such as a table) or oral suspension formulation comprising one or more lectins (e.g., BanLec or GRFT) and a pharmaceutically acceptable excipient or mixtures of excipients. In some embodiments, the oral composition or oral suspension formulation of the disclosure comprises one or more lectins (e.g., BanLec and/or GRFT) and oseltamivir phosphate and a pharmaceutically acceptable excipient or mixtures of excipients. In some embodiments, the oral composition or oral suspension formulation of the disclosure comprises one or more lectins (e.g., BanLec and/or GRFT) and a cannabinoid and a pharmaceutically acceptable excipient or mixtures of excipients. In some embodiments, the oral composition or oral suspension formulation of the disclosure comprises marine algae (e.g., *Gigartina* red algae) and a cannabinoid and a pharmaceutically acceptable excipient or mixtures of excipients.

In other embodiments, the oral composition or oral suspension formulation of the disclosure comprises marine algae (e.g., *Gigartina* red algae), one or more cannabinoids, and oseltamivir phosphate and a pharmaceutically acceptable excipient or mixtures of excipients. In other embodiments, the oral composition or oral suspension formulation of the disclosure comprises one or more lectins (e.g., BanLec and/or GRFT), one or more cannabinoids, and oseltamivir phosphate and a pharmaceutically acceptable excipient or mixtures of excipients.

The term "subject" as used herein refers to both human and non-human animals (e.g., domestic and farm animals, non-human primates, and zoo, sports or pet animals, such as dogs, horses, cats, and cows).

Lectins are sugar-binding proteins that are ubiquitous and can be found in microorganisms, plants, and animals. Lectins participate in many important cellular processes including cell-cell interactions and protein folding. Some lectins provide protection to the host from other organisms. Lectins have been developed widely as probes to investigate cell surface structure and functions; they have also found applications as antiviral drugs and in the delivery of chemotherapeutic agents. A number of lectins capable of binding the high-mannose glycans commonly found in the surface of the envelope glycoproteins. These lectins with cannabidiol can bind the viruses and prevent viral entry and fusion to target cells, thereby preventing infection or limit continued infection. Lectins can inhibit cell-cell fusion between chronically infected and uninfected cells and its efficacy as an antiviral agent against other enveloped viruses has also been shown.

Examples of lectins include, but are not limited to, Banana lectin (BanLec), griffithsin (GRFT), concanvalin A, lentil lectin, snowdrop lectin, ricin, peanut agglutinin, jacalin, *Vicia villosa* lectin (hairy vetch lectin), wheat germ agglutinin, elderberry lectin, *Maackia amurensis* leukoagglutinin, *Maackia amurensis* hemoagglutinin, *ulex europaeus* agglutinin, *aleuria aurantia* lectin, and mutants thereof. In some embodiment, the lectin can be isolated from marine algae (e.g., red algae, green algae, or brown algae) or seaweed.

GRFT has been shown to have antiviral activity against a number of enveloped viruses. Antiviral activity has nonetheless been attributed to carbohydrate-mediated binding to the respective viral envelope glycoproteins (Lusvarghi & Bewley (2016) *Viruses*, 8:296 1-18).

A list of effective concentrations of GRFT to inhibit 50% of virus infection ($EC_{50}$) is described in Table 2 of Lusvarghi & Bewley (2016) *Viruses*, 8:296 1-18, incorporated herein by reference.

An oral suspension formulation refers to compositions for oral use containing one or more active ingredients suspended in a suitable vehicle.

An oral suspension formulation of the disclosure can be capable of maintaining the active ingredients (e.g, a lectin, a sulfated polysaccharide, whole marine algae, a cannabinoid, and/or oseltamivir phosphate) in suspension so that the concentrations of the active ingredients are within ±10% when maintained at 15° C.-40° C. for at least about 90 days, or at least about 120 days, or at least about 180 days without shaking at any point during maintenance period.

Oseltamivir phosphate can be optionally combined with the compositions of the present disclosure. In some embodiments, the oral suspension formulation of the disclosure comprises oseltamivir phosphate at a concentration of 3 mg/mL-12 mg/mL (e.g., 3 mg/mL, 4 mg/mL, 5 mg/mL, 6 mg/mL, 7 mg/mL, 8 mg/mL, 9 mg/mL, 10 mg/mL, 11 mg/mL, or 12 mg/mL). In other embodiments, the oral suspension formulation comprises osteltamivir phosphate at a concentration of 6 mg/mL (or 60 mg per 360 ml for an oral suspension formula).

In some embodiments, the oral suspension formulation of the disclosure can comprise GRFT, BanLec, a cannabinoid, and/or oseltamivir phosphate, or combinations thereof.

In other embodiments, the compositions described herein can comprise 25 mg to 100 mg of osteltamivir phosphate (e.g., 25 mg, 30 mg, 45 mg, 50 mg, 60 mg, 75 mg, 80 mg, 85 mg, 90 mg, 95 mg, or 100 mg).

In some embodiments, the compositions of the present disclosure comprise a lectin (e.g., BanLec or GRFT) as an active ingredient. In some embodiments, the compositions described herein can comprise 25 mg to 100 mg of a lectin (e.g., 25 mg, 30 mg, 45 mg, 50 mg, 60 mg, 75 mg, 80 mg, 85 mg, 90 mg, 95 mg, or 100 mg).

In other embodiments, the active ingredients are a lectin combined with oseltamivir phosphate. In other embodiments, the active ingredients are sulfated polysaccharides from red algae (e.g., *Gigartina*) and oseltamivir phosphate. In other embodiments, the active ingredients are one or more lectins and/or one or more cannabinoids combined with oseltamivir phosphate. In other embodiments, the active ingredients are one or more red algae and/or one or more cannabinoids combined with oseltamivir phosphate.

Oral suspension formulations of the disclosure can comprise a lectin (e.g., GRFT or BanLec) in a concentration of about 3 mg/mL-12 mg/mL (e.g., 3 mg/mL, 4 mg/mL, 5 mg/mL, 6 mg/mL, 7 mg/mL, 8 mg/mL, 9 mg/mL, 10 mg/mL, 11 mg/mL, or 12 mg/mL). In some embodiments, the composition comprises a lectin in a concentration of 60 mg per 360 ml. Solid dosage forms of the disclosure can comprise a lectin (e.g., GRFT or BanLec) in an amount of about 30 mg-100 mg (e.g., 30 mg, 40 mg, 50 mg, 60 mg, 70 mg, 80 mg, 90 mg, 100 mg). In some embodiments, the compositions of the present disclosure comprises one or more lectins (e.g., GRFT, BanLec, or GRFT and BanLec).

Oral suspension formulations of the disclosure can comprise a sulfated polysaccharide in a concentration of about 3 mg/mL-12 mg/mL (e.g., 3 mg/mL, 4 mg/mL, 5 mg/mL, 6 mg/mL, 7 mg/mL, 8 mg/mL, 9 mg/mL, 10 mg/mL, 11 mg/mL, or 12 mg/mL). Oral suspension formulations of the disclosure can comprise whole marine algae (e.g., *Gigartina* red algae) in a concentration of about 3 mg/mL-12 mg/mL (e.g., 3 mg/mL, 4 mg/mL, 5 mg/mL, 6 mg/mL, 7 mg/mL, 8 mg/mL, 9 mg/mL, 10 mg/mL, 11 mg/mL, or 12 mg/mL). In some embodiments, the oral suspension formulation comprises whole marine algae (e.g., *Gigartina* red algae) in a concentration of 60 mg per 360 ml. Solid dosage forms of the disclosure can comprise whole marine algae (e.g., red algae) in an amount of about 20 mg-100 mg (e.g., 20 mg, 30 mg, 40 mg, 50 mg, 60 mg, 70 mg, 80 mg, 90 mg, 100 mg). In some embodiments, the compositions of the present disclosure comprises one or more sulfated polysaccharides from red algae or one or more species of marine algae (e.g., two or more different species of red algae or a combination of green and red algae).

In some embodiments of the present disclosure, the compositions can comprise one or more lectins and one or more cannabinoids and/or oseltamivir phosphate.

In other embodiments of the present disclosure, the compositions can comprise one or more species of red algae and one or more cannabinoids. In other embodiments of the present disclosure, the compositions can comprise one or more sulfated polysaccharides and one or more cannabinoids.

Sulfated polysaccharides are negatively charged polysaccharides that can be found in the cell wall of seaweed or marine algae. Sulfated polysaccharides can be isolated from green algae, red algae, brown algae, yellow-green algae, fire algae, golden-brown algae, and/or euglenoids. In particular, sulfated polysaccharides can be isolated from algal genera of *Phaeophyta*, *Rhodophyta*, and *Chlorophyte*. Sulfated polysaccharides can also be contained in dried whole marine algae (e.g, red algae).

Examples of green algae include, but are not limited to, *Dunaliella salina*, *Ulva* (e.g., *Ulva armoricana*, *Ulva lactuca*, *Ulva rigida*), *Enteromorpha*, *Monostroma* (e.g., *Monostroma latissimum*, *Monostroma nitidum*), *Caulerpa* (e.g., *Caulerpa racemose*), *Codium* (e.g., *Codium fragile*, *Codium vermilara*), *Gayralia* (e.g., *Gayralia oxysperma*).

Examples of red algae include, but are not limited to, *Gracilaria* (e.g., *Gracilaria birdiae*, *Gracilaria cornea*), *Gigartina* (e.g., *Gigartina skottsbergii*, *Gigartina atropurpurea*), *Gelidium* (e.g., *Gelidium crinale*), *Lomentaria* (e.g., *Lomentaria catenata*), *Corallina* (e.g., *Corallina officinalis*, *Corallina sertularioide*), *Champia* (e.g., *Champia feldmannii*), *Solieria* (e.g., *Solieria filiformis*), *Gyrodinium* (e.g., *Gyrodinium impudium*), *Nemalion* (e.g., *Nemalion helminthoides*), *Sphaerococcus* (e.g., *Sphaerococcus coronopifolius*), *Boergeseniella* (e.g., *Boergeseniella thuyoides*), *Sebdenia* (e.g., *Sebdenia polydactyla*), *Scinaia*, *Cyanidioschyzon merolae*, *Atractophora hypnoides*, *Gelidiella calcicola*, *Lemanea*, *Palmaria palmata*, *Schmitzia hiscockiana*, *Chondrus* (e.g., *Chondrus crispus*), *Mastocarpus stellatus*, *Vanvoorstia bennettiana*, *Acrochaetium efflorescens*, *Audouinella*, *Polysiphonia ceramiaeformis*, *Vertebrata simulans*, *Hypnea*, *Grateloupia indicia*, *Schizymenia binderi*, *Kappaphycus alvarezii* or *Eucheuma*.

Examples of brown algae include, but are not limited to, *Ascophyllum*, *Canistrocarpus*, *Dictyopteris*, *Dictyota*, *Eclonia*, *Ecklonia maxima*, *Lobophota*, *Sargassum*, *Laminaria* (e.g., *Laminaria angustata*), *Adenocystis* (e.g., *Adenocytis utricularis*), *Fucus*, *Sphacelaria* (e.g., *Sphacelaria indicia*), *Cystoseira* (e.g., *Cystoseira indicia*), *Undaria*, *Lessonia* (e.g., *Lessonia vadosa*), *Padina*, or *Turbinaria*, Examples of sulfated polysaccharides include, but are not limited to, fucan, fucoidan, carrageenan, galactan, agaran, ulvan, heparin, heparin sulfate, fucoidam, glycosaminoglycans, galactofucan, mannoglucuronofucan, oligosaccharides, arabinogalactan, rhamnam, mannas, heterorhamnan, xylomannan sulfate, xylogalactofucan, and xylomannan.

In some embodiments, the sulfated polysaccharides of the present disclosure are isolated from *Gigartina* red algae.

In other embodiments of the disclosure, the compositions comprise whole marine algae, such as red algae *Gigartina*, that have been dried (e.g., freeze dried or lyophilized) and contain sulfated polysaccharides. Dried marine algae (e.g., red algae *Gigartina*) can be dried for use in the compositions of the disclosure by processes known in the art (e.g., sun, shade, oven, vacuum, and freeze-drying techniques). In some embodiments, the compositions of the present disclosure can contain a mixture of marine algae species (e.g., one or more species of red algae or a combination of red and green algae species).

In some embodiments, the compositions comprise about 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg of dried marine algae (e.g., red algae) that contains one ore more sulfated polysaccharides.

The compositions of the disclosure comprise cannabinoids. Examples of a cannabinoid include, but are not limited to, compounds belonging to any of the following classes of molecules, their derivatives, salts, or analogs: tetrahydrocannabinols (THCs), including delta-9-tetrahydrocannabivarin (THCv), 10-Ethoxy-9-hydroxy-delta-6a-tetrahydrocannabinol, 8,9-dihydroxy-delta-6a-tetrahydrocannbinol, delta-8-tetrahydrocannbinol, delta-8-tetrahydrocannbinolic acid, delta-9-tetrahydrocannbinol-C4 (THC-C4), delta-9-tetrahydrocannbinoic acid A (THCA-A), delta-9-tetrahydrocannbinolic acid B (THCA-B), delta-9-tetrahydrocannbinolic acid-C4 (THCA-C4), delta-9-tetrahydrocannabiorcol (THC-C1), delta-9-tetrahydrocannabiorolic acid (THCA-C1), delta-9-tetrahydrocannabivarinic acid (THCVA), 10-Oxo-delta-6a-tetrahydrocannbinol (OTHC), dehydrocannbifuran (DCBF), delta-9-cis-tetrahydrocannabinol (cis-THC), trhydroxy-delta-9-tetrahydrocannabinol (triOH-THC), 3,4,5,6,-tetrahydro-7-hydroxy-alpha-alpha-2-trimethyl-9-n-propyl-2, or cannabidiols (CBDs), including cannabinol (CBN), cannabichromene (CBC), cannabichromenic acid (CBCA), cannabicyclol (CBL), cannabicyclolic acid (CBLA), cannabicyclovarin (CBLV), cannabivarin (CBV), Cannabidivarin (CBDVa), cannabinodiol (CBND), cannabielsion (CBE), cannabicyclol (CBL), cannabicyloic acid (CBLA), cannabitriol (CBT), cannabidiol monomehylerther (CBDM), cannabidiolic acid (CBDA), cannabidiorcol (CBD-C1), cannabielsoic acid B (CBEA-B), cannabielsin (CBE), cannabielsoin acid A (CBEA-A), cannabigerol (CBG), cannabigerol monomethlether (CBGM), cannabigerolic acid (CBGA), cannabigerolic acid (CBGA), cannabigerolic acid monomethlether (CBGAM), cannabigerovarin (CBGV), cannabigerovarinic acid (CBGVA), cannabinodiol (CBND), cannabinodivarin (CBVD), cannabinol (CBN), cannabinol methlether (CBNM), Cannabinol-C2 (CBN-C2), Cannabinol-C4 (CBN-C4), cannabinolic acid (CBNA), cannabiorcool (CBN-C1), cannabivarin (CBV), cannaitriol (CBT), cannabitriolvarin (CBTV), cannabichromanon (CBCF), cannabifuran (CBF), cannabiglendol (OH-iso-HHCV), cannabiripsol (CBR), cannbicitran (CBT), 6-methano-2H-1-benzoxocin-5-methanol, and iso-canabinoids. Examples of non-psychoactive cannabinoids include, but are not limited to, CBD, CBC, CBE, CBG, CBN, CBND, CBT, CBDV, CBGV, and CBCV.

In some embodiments, the cannabinoid is cannabidiol (CBD). In some embodiments, the cannabinoid is a hemp-derived cannabidiol. The term "hemp" as used herein refers to a *Cannabis* plant that contains less than 0.3% THC on a dry weight basis. In other embodiments, the hemp-derived cannabidiol is derived from a specific tested cultivator and strain as disclosed in U.S. patent application Ser. No. 16/501,096. In some embodiments, the cannabinoid derived from hemp is CBD or CBG.

In other embodiments, the composition can contain about 25 mg to about 100 mg of cannabinoid per composition (e.g., tablet or oral suspension).

In another embodiment, the composition can contain about 25.0 mg, 25.1 mg, 25.2 mg, 25.3 mg, 25.4 mg, 25.6 mg, 25.7 mg, 25.8 mg, 25.9 mg, 26.0 mg, 26.1 mg, 26.2 mg, 26.3 mg, 26.4 mg, 26.5 mg, 26.6 mg, 26.7 mg, 26.8 mg, 26.9 mg, 27.0 mg, 27.1 mg, 27.2 mg, 27.3 mg, 27.4 mg, 27.5 mg, 27.6 mg, 27.7 mg, 27.8 mg, 27.9 mg, 28.0 mg, 28.1 mg, 28.2 mg, 28.3 mg, 28.4 mg, 28.5 mg, 28.6 mg, 28.7 mg, 28.8 mg, 28.9 mg, 29.0 mg, 29.1 mg, 29.1 mg, 29.3 mg, 29.4 mg, 29.5 mg, 29.6 mg, 29.7 mg, 29.8 mg, 29.9 mg, 30.0 mg, 30.1 mg, 30.2 mg, 30.3 mg, 30.4 mg, 30.5 mg, 30.6 mg, 30.7 mg, 30.8 mg 30.9 mg, 31.0 mg, 31.1 mg, 31.2 mg, 31.3 mg, 31.4 mg, 31.5 mg, 31.6 mg, 31.7 mg, 31.8 mg, 31.9 mg, 32.0 mg, 32.1 mg, 32.2 mg, 32.3 mg, 32.4 mg, 32.5 mg, 32.6 mg, 32.7 mg, 32.8 mg, 32.9 mg, 33.0 mg, 33.1 mg, 33.2 mg, 33.3 mg, 33.4 mg, 33.5 mg, 33.6 mg, 33.7 mg, 33.8 mg, 33.9 mg, 34.0 mg, 34.1 mg, 34.2 mg, 34.3 mg, 34.5 mg, 34.6 mg, 34.7 mg, 34.8 mg, 34.9 mg, or 35.0 of a cannabinoid (e.g., CBD).

In other embodiments, the composition can comprise about 25 mg to about 120 mg of a cannabinoid (e.g., CBD). For example, the composition can comprise about 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, or 120 mg of a cannabinoid.

In some embodiments, the composition is in the form of a dissolvable sublingual tablet. As used herein, the term sublingual means "under the tongue" as a route of administering the composition.

In some embodiments, the composition is in the form of an orally dissolvable tablet, which can be dissolved when placed in any part of the mouth.

In other embodiments, the composition is in the form of a chewable tablet.

As used herein, the term "rapidly dissolving oral composition" refers to a composition that can completely disintegrate in the oral cavity of a subject when the composition comes in contact with saliva. A rapidly dissolving oral composition can be placed in the mouth where it disperses rapidly before swallowing and which disintegrates in 3 minutes or less (e.g., the tablet disintegrates or dissolves in about 280 seconds, 260 seconds, 240 seconds, 220 seconds, 200 seconds, 180 seconds, 160 seconds, 140 seconds, 120 seconds, 100 seconds, 80 seconds, 60 seconds, 59 seconds, 58 seconds, 57 seconds, 56 seconds, 55 seconds, 54 seconds, 53 seconds, 52 seconds, 51 seconds, 50 seconds, 49 seconds, 48 seconds, 47 seconds, 46 seconds, 45 seconds, 44 seconds, 43 seconds, 42 seconds, 41 seconds, 40 seconds, 39 seconds, 38 seconds, 37 seconds, 36 seconds, 35 seconds, 34 seconds, 33 seconds, 32 seconds, 30 seconds, 25 seconds, or 20 seconds). In some embodiments, the rapidly dissolving oral composition dissolves in 60 seconds or less.

The rapidly dissolving oral composition can also dissolve by being placed on or under the tongue or swallowed.

A rapidly dissolving oral composition can include, but is not limited to, compositions referred to as orodispersibles, rapimelts, quick dissolving compositions, rapid disintegrating compositions, mouth dissolving compositions, oral lyophilisates, melt-in-mouth compositions, mouth dispersing compositions, fast mouth dissolving compositions, fast melting compositions, porous tablets, orodispersing tablets.

In some embodiments, the rapidly dissolving oral composition is a tablet.

A rapidly dissolving oral composition of the disclosure can be evaluated according to following features using methods known in the art: wetting time, hardness, friability test, mechanical strength, uniformity of dispersion, water absorption ratio, taste/mouth sensation, in vitro and in vivo disintegration test, in-vitro dissolution test and stability studies and moisture uptake studies. The rapidly dissolving oral composition can also be evaluated for organoleptic features, such as taste-masking properties or having a taste that is sweet. In some embodiments, the rapidly dissolving oral composition is tasteless.

In some embodiments, the rapidly dissolving oral composition contains about 2 mg to about 150 mg (e.g., 2 mg, 3 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, or 150 mg) of cannabinoid per composition (e.g., per tablet). In some embodiments, the rapidly dissolving oral composition can have a total weight of about 100 mg to about 750 mg.

In some embodiments, the solid dosage composition has a total weight of about 100 mg to about 800 mg, about 550 mg to about 625 mg, about 630 mg to about 705 mg, about 627 mg to about 702 mg, or about 600 mg to about 1000 mg. In some embodiments, the composition has a total weight of about 120 mg. In some embodiments, the composition is in the form of a tablet having a total weight of 120 mg.

In some embodiments, the compositions of the disclosure can comprise a terpene. The term "terpene" as used herein refers to an organic compound that is derived biosynthetically from units of isopentenyl pyrophosphate. Terpene molecules found in plants can be the primary constituents of essential oils and can produce fragrances and smells. Terpenes can be monoterpenoids, sesquiterpenoids, sesterterpenoid, sesquarterpenoids, tetraterpenoids, Triterpenoids, tetraterpenoids, Polyterpenoids, isoprenoids, and steroids. Terpenes can be: α-, β-, γ-, oxo-, isomers, or combinations thereof. Examples of terpenes include, but are not limited to, 8-dihydroionone, Acetanisole, Acetic Acid, Acetyl Cedrene, Anethole, Anisole, Benzaldehyde, Bergamotene (α-cis-Bergamotene, α-trans-Bergamotene), Bisabolol (β-Bisabolol, α-Bisabolol), Borneol, Bornyl Acetate, Butanoic/Butyric Acid, Cadinene (α-Cadinene, γ-Cadinene), Cafestol, Caffeic acid, Camphene, Camphor, Capsaicin, Carene (A-3-Carene, delta-3-Carene), Carotene, Carvacrol, Carvone, Dextro-Carvone, Laevo-Carvone, Caryophyllene (β-Caryophyllene), Caryophyllene oxide, Castoreum Absolute, Cedrene (α-Cedrene, β-Cedrene), Cedrene Epoxide (α-Cedrene Epoxide), Cedrol, Cembrene, Chlorogenic Acid, Cinnamaldehyde (α-amyl-Cinnamaldehyde) (α-hexyl-Cinnamaldehyde), Cinnamic Acid, Cinnamyl Alcohol, Citronellal, Citronellol, Cryptone, Curcumene (α-Curcumene, γ-Curcumene), Decanal, Dehydrovomifoliol, Diallyl Disulfide, Dihydroactinidiolide, Dimethyl Disulfide, Eicosane/Icosane, Elemene (8-Elemene), Estragole, Ethyl acetate, Ethyl Cinnamate, Ethyl maltol, Eucalyptol/1,8-Cineole, Eudesmol (α-Eudesmol, β-Eudesmol, γ-Eudesmol), Eugenol, Euphol, Farnesene, Farnesol, Fenchol (β-Fenchol), Fenchone, Geraniol, Geranyl acetate, Germacrenes, Germacrene B, Guaia-1(10), 11-diene, Guaiacol, Guaiene (α-Guaiene), Gurjunene (α-Gurjunene), Herniarin, Hexanaldehyde, Hexanoic Acid, Humulene (α-Humulene, β-Humulene), Ionol (3-oxo-α-ionol, 13-Ionol), Ionone (α-Ionone, β-Ionone), Ipsdienol, Isoamyl acetate, Isoamyl Alcohol, Isoamyl Formate, Isoborneol, Isomyrcenol, Isopulegol, Isovaleric Acid, Isoprene, Kahweol, Lavandulol, Limonene, γ-Linolenic Acid, Linalool, Longifolene, α-Longipinene, Lycopene, Menthol, Methyl butyrate, 3-Mercapto-2-Methylpentanal, Mercaptan/Thiols, β-Mercaptoethanol, Mercaptoacetic Acid, Allyl Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (p-Myrcene, β-Myrcene), γ-Muurolene, Nepetalactone, Nerol, Nerolidol, trans-Nerolido, Neryl acetate, Nonanaldehyde, Nonanoic Acid, Ocimene, Octanel, Octanoic Acid, P-cymene, Pentyl butyrate, Phellandrene, Phenylacetaldehyde, Phenylethanethiol, Phenylacetic Acid, Phytol, Pinene (α-Pinene, β-Pinene), Propanethiol, Pristimerin, Pulegone, Quercetin, Retinol, Rutin, Sabinene, Sabinene Hydrate, cis-Sabinene Hydrate, trans-Sabinene Hydrate, Safranal, α-Selinene, α-Sinensal, β-Sinensal, β-Sitosterol, Squalene, Taxadiene, Terpin hydrate, Terpineol, Terpine-4-ol, α-Terpinene, γ-Terpinene, Terpinolene, Thiophenol, Thuj one, Thymol, α-Tocopherol, Tonka Undecanone, Undecanal, Valeraldehyde/Pentanal, Verdoxan, α-Ylangene, or Umbelliferone. In some embodiments, the composition comprises 25 mg to 100 mg of a terpene (e.g., 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg).

The oral composition can comprise a cannabinoid and a pharmaceutically acceptable excipient or mixtures of excipients.

An excipient is a substance formulated alongside the active ingredient of a composition that can confer a therapeutic enhancement of the active ingredient (e.g., improving disintegration of the composition). Excipients can include a variety of different types of ingredients, including but not limited to, antiadherents, binders, coatings, colors, diluents, disintegrants, fillers, flavors, glidants, lubricants, preservatives, sorbents, and taste enhancing agents. As used herein, non-cannabinoid ingredients may be referred to generally as an excipient or identified as a type of excipient (e.g., a disintegrant or glidant). It will be appreciated that certain excipients can be categorized as more than one type of excipient (e.g., magnesium stearate is an excipient that can be used as a lubricant or antiadherent).

Acceptable excipients can include, but are not limited to, calcium sulfate, starch, mannitol, kaolin, sorbitol, xylitol, sodium chloride, sodium bicarbonate, citric acid, powdered cellulose derivatives, microcrystalline cellulose, pullulan, silicified microcrystalline cellulose, ammonium bicarbonate, carrageenan, carbohydrates such as Pharmaburst™ (SPI Pharma Inc., New Castle, Del.), magnesium carbonate, tribasic calcium phosphate, calcium sulfate, magnesium oxide, poloxamer, gums, hydroxypropyl methylcellulose, gelatin, and mixtures thereof.

In some embodiments, the excipient is a co-processed carbohydrate. In other embodiments, the excipient is a co-processed carbohydrate containing mannitol and sorbitol in a 2:1 ratio. The co-processed carbohydrate system of the disclosure can refer to the system described in U.S. Pat. No. 7,118,765, incorporated herein by reference. In particular, the term "co-processed carbohydrate" as used herein refers to the processing of at least two polyols together to make a single product. For example, mannitol and sorbitol can be co-spray dried by first preparing a single solution of mannitol and sorbitol. The term "co-processed carbohydrate system" can include a co-processed carbohydrate plus a disintegrant and a glidant. The term "co-processed carbohydrate system formulation or composition" can include the co-processed carbohydrate system plus one or more cannabinoids to be formed into a tablet.

Disintegrants expand and dissolve when wet (e.g., contacted by saliva) causing an oral dosage form (e.g., tablet) to break apart and release the active ingredients. Disintegrants can help the oral dosage form to rapidly dissolve. Acceptable disintegrants include, but are not limit to, crospovidone, sodium starch glycolate, sodium carboxymethyl cellulose, calcium carboxymethyl cellulose, croscarmellose sodium, alginic acid, chitosan, methyl cellulose, microcrystalline cellulose, powdered cellulose, lower alkyl substituted hydroxypropyl cellulose, polacrilin potassium, starch, pregelatinized starch, sodium alginate, or combinations thereof.

Glidants are used to promote powder flow by reducing interparticle friction and cohesion. Glidants can be used in combination with lubricants. Acceptable glidants include, but are not limited to, colloidal silica, silica gel, precipitated silica, silicon dioxide, colloidal silicon dioxide, calcium silicate, magnesium silicate, magnesium trisilicate, talc, starch, or combinations thereof.

In some embodiments, the composition further comprises a taste enhancing agent and a lubricant.

Taste enhancing agents can help an oral dosage form become more palatable and can mask unpleasant organoleptic properties (e.g., taste and smell) of the ingredients contained in the compositions. Acceptable taste enhancing agents include, but are not limited to, sucralose, tagatose, aspartame, acesulfame potassium, saccharin, neotame, acesulfame K, and the like, or combinations thereof. Adding taste enhancing agents to the compositions of the present disclosure can also result in a composition that has no appreciable taste or is tasteless.

In other embodiments, the composition is tasteless. A tasteless composition lacks a taste or flavor. A tasteless composition can have little or no taste during the entire consumption period. For example, if the composition is a tablet, a tasteless tablet can have little to no taste over the entire course of time that it takes for the table to dissolve (e.g., in the mouth or on or under the tongue) or be swallowed by the subject. A tasteless composition can also have little or no aftertaste once the composition has been dissolved or swallowed.

In some embodiments, the disintegration mix of molecule binding leads to no taste in the composition. A tasteless composition of the present disclosure can contain an inert powder that comprises sorbitol, mannitol, isomalt, and a disintegrate (crospovidone) that causes the composition to be tasteless.

Lubricants can prevent ingredients from clumping together and from sticking to tableting machines. Acceptable lubricants include, but are not limited to, calcium stearate, glyceryl monostearate, glyceryl behenate, glyceryl palmitostearate, hydrogenated vegetable oil, light mineral oil, magnesium stearate, mineral oil, polyethylene glycol, poloxamer, sodium benzoate, sodium lauryl sulfate, sodium stearyl fumarate, stearic acid, talc, zinc stearate, and mixtures thereof.

In some embodiments, the excipient or mixture of excipients comprises one or more sugar alcohols (e.g., mannitol, sorbitol, xylitol, lactitol, or maltitol).

As used herein, the term "direct compression molecular binding" refers to using binder excipients that have the ability to be compressed into a tablet or other similar oral dosage form directly from powdered active and inactive ingredients. Tablet binders are used in formulating a solid oral dosage form and serve to hold the active and inactive ingredients together in a cohesive mix. Acceptable binders include, but are not limited to, saccharides and their derivatives, sucrose, lactose, starches, cellulose, methyl cellulose, polyvinlypyrrolidone, polyethylene glycol, xylitol, sorbitol, mannitol, or gelatin. Dry binders are added to a powder blend, either following a wet granulation step or as part of a direct powder compression formula.

Another aspect of the disclosure provides a method for preparing a tablet: (i) preparing a mixture of powder comprising active ingredients (e.g., lectins, marine algae, and cannabinoids); (ii) blending the ingredients prepared in step (i) with tableting excipients; and (iii) compressing the blend of step (ii) into a tablet.

The term "tableting excipients" as used herein refers to any excipients used to form a tablet. The tableting excipients can include, for example, a filler, a binder, a taste enhancing agent, a disintegrant, and a lubricant. A filler can be any pharmaceutically acceptable filler or diluent, including, but not limited to lactose, starch, dextrose, sucrose, fructose, maltose, mannitol, sorbitol, kaolin, microcrystalline cellulose, powdered cellulose or any combination thereof. The filler can consist of a mixture of water soluble fillers to reduce the chance of unpleasant grittiness when the tablet dissolves in the oral cavity of the patient. The filler can also be a direct compression sugar such as confectioners sugar, dextrates, dextrin, dextrose, fructose, maltose, mannitol, polydextrose, sorbitol, or other sugars and sugar derivatives.

A disintegrant can be an agent that causes oral dosage forms (e.g., tablets) to disintegrate and release their medicinal substances on contact with moisture (e.g., saliva). Disintegrants include, but are not limited to, crosslinked polymers, such as crosslinked polyvinylpyrrolidone (crospovidone), crosslinked sodium carboxymethyl cellulose (croscarmellose sodium), and sodium starch glycolate.

In some embodiments, the tableting excipient is a co-processed carbohydrate containing mannitol and sorbitol in a 2:1 ratio.

It will be appreciated that the tableting method can be used with a variety of different weights of starting materials, and the methods described herein can be scaled up or down to produce the final compositions using methods known in the art.

Friability of the Formulations. Afriability value of about 1 percent or less is desirable for tablets in order for them to withstand the stress of handling during production, packaging and transport. The formulations described herein can achieve low friability levels. Friability remains low, and even decreases as tablet hardness increased. Co-spray dried carbohydrate system achieves a much lower friability percent as compared with the same ingredients prepared as dry blends.

Disintegration Times in Oral Cavity for Different formulations. Disintegration time can range from about 30 seconds to about 60 seconds varying with tablet hardness up to about 8 KP. Over-the-counter quick dissolve tablets provide a reference point having a tablet hardness of about 1.5 KP and a disintegration time of about 42 seconds.

Example 1: Lectin and Cannabinoid Oral Suspension Formulation

An oral suspension formulation of the present disclosure can comprise GRFT in a concentration of 6 mg/mL, BanLec at a concentration of 6 mg/mL, CBD in a concentration of 20 mg/ml to 50 mg/mL, a buffering agent (e.g., monosodium phosphate and or disodium phosphate), optionally, a taste enhancing agent, and purified water. The formulation can also optionally contain osteltamivir phosphate at a concentration of 6 mg/mL. The oral suspension formulation can be stable at room temperature 15°-30° Celsius. The oral suspension formulation can be consumed by swallowing.

Example 2: Lectin and Cannabinoid Oral Tablet

A tablet of the present disclosure can have a composition as described in Tables 1-2. The tablet can be made with or without sucralose (a sweetener). The tablet can be consumed by placing the tablet under the tongue where it dissolves.

TABLE 1

Tablet Formulation #1

| Ingredient | mg/tablet | % (w/w) |
| --- | --- | --- |
| Co-processed carbohydrate excipient | 500 mg | 80-71 |
| Mannitol/Sorbitol | 67.5 mg | 11-10 |
| BanLec | 30-100 mg | 5-14 |
| Cannabinoid (e.g., CBD) | 27.5-32.5 mg | 4-5 |
| Sweetener (sucralose) | 3 mg | 5-0.4 |
| Lubricant (sodium Stearyl fumarate) | 2 mg | 0.3 |
| Total Tablet Weight | 630 mg-705 mg | 100 |

TABLE 2

Tablet Formulation #2

| Ingredient | mg/tablet | % (w/w) |
| --- | --- | --- |
| Co-processed carbohydrate excipient | 500 mg | 80-71 |
| Mannitol/Sorbitol | 67.5 mg | 11-10 |
| BanLec | 30-100 mg | 5-14 |
| Cannabinoid (e.g., CBD) | 27.5-32.5 mg | 4-5 |
| Lubricant (sodium Stearyl fumarate) | 2 mg | 0.3 |
| Total Tablet Weight | 627 mg-702 mg | 100 |

Example 3: Sulfated Polysaccharide and Cannabinoid Oral Tablet

A tablet of the present disclosure can have a composition as described in Table 3. This composition can be in the form of a sublingual dissolvable tablet. The tablet can be consumed by placing it under the tongue where it dissolves. The tablet can also be tasteless.

TABLE 3

Tablet Formulation

| Ingredient | mg/tablet | % (w/w) |
| --- | --- | --- |
| *Gigartina* Red Algae | 30 | 25 |
| Cannabinoid (CBD) | 30 | 25 |
| Co-processed carbohydrate excipient | 58 | 48 |
| Lubricant (magnesium stearate) | 2 | 2 |
| Total Tablet Weight | 120 mg | 100 |

Any patents or publications mentioned in this specification are indicative of the levels of those skilled in the art to which the disclosure pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present disclosure is well adapted to carry out the objects and obtain the ends and advantages mentioned, as well as those inherent therein. The present disclosure described herein is presently representative of preferred embodiments and is not intended as limitations on the scope of the disclosure. Changes therein and other uses will occur to those skilled in the art which are encompassed within the spirit of the disclosure as defined by the scope of the claims.

The invention claimed is:

1. An oral composition comprising:
   i) a sulfated polysaccharide contained in *Gigartina* whole red algae;
   ii) a cannabinoid; and
   iii) a pharmaceutically acceptable excipient,
   wherein the amounts of the *Gigartina* whole red algae and the cannabinoid are about the same, and wherein the composition is in the form of a tablet.

2. The composition of claim 1, wherein the *Gigartina* whole red algae is *Gigartina skottsbergii* or *Gigartina atropurpurea*.

3. The composition of claim 1, wherein the cannabinoid is tetrahydrocannabinol (THC), delta-9-tetrahydrocannabivarin (THCv), 10-Ehtoxy-9-hydroxy-delta-6a-tetrahydrocannabinol, 8,9-dihydroxy-delta-6a-tetrahydrocannbinol, delta-8-tetrahydrocannabinol, delta-8-tetrahydrocannabinolic acid, delta-9-tetrahydrocannabinol-C4 (THC-C4), delta-9-tetrahydrocannabinoic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorolic acid (THCA-C1), delta-9-tetrahydrocannabivarinic acid (THCVA), 10-Oxo-delta-6a-tetrahydrocannbinol (OTHC), dehydrocannbifuran (DCBF), delta-9-cis-tetrahydrocannabinol (cis-THC), trhydroxy-delta-9-tetrahydrocannabinol (triOH-THC), 3,4,5,6,-tetrahydro-7-hydroxy-alpha-alpha-2-trimethyl-9-n-propyl-2, cannabidiol (CBD), cannabinol (CBN), cannabichromene (CBC), cannabichromenic acid (CBCA), cannabicyclol (CBL), cannabicyclolic acid (CBLA), cannabicyclovarin (CBLV), cannabivarin (CBV), Cannabidivarin (CBDVa), cannabinodiol (CBND), cannabielsion (CBE), cannabicyclol (CBL), cannabicyloic acid (CBLA), cannabitriol (CBT), cannabidiol monomehylerther (CBDM), cannabidiolic acid (CBNA), cannabidiorcol (CBD-C1), cannabielsoic acid B (CBEA-B), cannabielsin (CBE), cannabielsoin acid A (CBEA-A), cannabigerol (CBG), cannabigerol monomethiether (CBGM), cannabigerolic acid (CBGA), cannabigerolic acid (CBGA), cannabigerolic acid monomethiether (CBGAM), cannabigerovarin (CBGV), cannabigerovarinic acid (CBGVA), cannabinodiol (CBND), cannabinodivarin (CBVD), cannabinol (CBN), cannabinol methlether (CBNM), cannabinol-C2 (CBN-C2), cannabinol-C4 (CBN-C4), cannabinolic acid (CRNA), cannabiorcool (CBN-C1), cannabivarin (CBV), cannaitriol (CBT), cannabitriolvarin (CBTV), cannabichromanon (CBCF), cannabifuran (CBF), cannabiglendol (OH-iso-HHCV), cannabiripsol (CBR), cannbicitran (CBT), or 6-methano-2H-1-benzoxocin-5-mehtnaol or combinations thereof.

4. The composition of claim 1, wherein the cannabinoid is a cannabidiol isolate or tetrahydrocannabinol isolate.

5. The composition of claim 1, wherein the cannabinoid is a hemp-derived cannabidiol.

6. The composition of claim 1, wherein the amount of cannabinoid is from about 25 mg to about 35 mg.

7. The composition of claim 1, wherein the cannabinoid is a mixture of one or more cannabinoids.

8. The composition of claim 1, wherein the amount of *Gigartina* whole red algae is about 25 mg to about 35 mg.

9. The composition of claim 1, wherein the excipient is a co-processed carbohydrate containing mannitol and sorbitol in a 2:1 ratio.

10. The composition of claim 1, wherein the composition further comprises a taste enhancing agent and a lubricant.

11. The composition of claim 1, wherein the excipient comprises one or more sugar alcohols.

12. The composition of claim 1, wherein the tablet dissolves in the oral cavity.

13. The composition of claim 1, wherein the total weight of the tablet is about 100 rags to about 750 mgs.

14. The composition of claim 1, wherein the composition is tasteless.

15. The composition of claim 1, wherein the composition further comprises oseltamivir phosphate.

16. The composition of claim 1, wherein the *Gigartina* whole red algae is dried.

\* \* \* \* \*